US008846911B2

(12) United States Patent
Maillard et al.

(10) Patent No.: US 8,846,911 B2
(45) Date of Patent: Sep. 30, 2014

(54) PROCESS OF ISOLATING ENANTIOMER COMPONENTS FROM ENANTIOMER MIXTURES BY PARTICLE-SIZE-CONTROLLED CRYSTALLIZATION

(71) Applicants: David Maillard, Darmstadt (DE);
Guntram Koller, Klein-umstadt (DE);
Ewgenij Wakaresko, Aschaffenburg (DE); Sabine Gottburg-Reininger, Darmstadt (DE)

(72) Inventors: David Maillard, Darmstadt (DE);
Guntram Koller, Klein-umstadt (DE);
Ewgenij Wakaresko, Aschaffenburg (DE); Sabine Gottburg-Reininger, Darmstadt (DE)

(73) Assignee: Poxel, Lyons (FR)

( * ) Notice: Subject to any disclaimer, the term of this patent is extended or adjusted under 35 U.S.C. 154(b) by 0 days.

(21) Appl. No.: 13/975,744

(22) Filed: Aug. 26, 2013

(65) Prior Publication Data
US 2013/0345421 A1 Dec. 26, 2013

Related U.S. Application Data

(62) Division of application No. 12/737,613, filed as application No. PCT/EP2009/059769 on Jul. 28, 2009.

(30) Foreign Application Priority Data

Jul. 29, 2008 (EP) .................................. 08013586

(51) Int. Cl.
| | | |
|---|---|---|
| *C07D 251/10* | (2006.01) | |
| *C07B 57/00* | (2006.01) | |
| *C07C 29/78* | (2006.01) | |
| *C07D 251/08* | (2006.01) | |

(52) U.S. Cl.
CPC ........... *C07D 251/08* (2013.01); *C07B 2200/07* (2013.01); *C07B 57/00* (2013.01); *C07C 29/78* (2013.01); *C07D 251/10* (2013.01)
USPC ............ 544/204; 544/206; 544/208; 544/209

(58) Field of Classification Search
CPC .............................. C07D 251/10; C07B 57/00
USPC .................................. 544/204, 206, 208, 209
See application file for complete search history.

(56) References Cited

U.S. PATENT DOCUMENTS

| | | | |
|---|---|---|---|
| 7,501,511 B2 * | 3/2009 | Moinet et al. ................. | 544/206 |
| 2006/0223803 A1 | 10/2006 | Moinet et al. | |
| 2011/0184169 A1 | 7/2011 | Maillard | |

FOREIGN PATENT DOCUMENTS

WO    WO 2004/089917    10/2004

OTHER PUBLICATIONS

International Search Report for PCT/EP2009/059769, mailed Jun. 22, 2010.
Collet, A. et al.; "Optical Resolution by Direct Crystalliztion of Enantiomer Mixtures", Chemical Reviews, vol. 80, No. 3, (Jun. 1980), pp. 215-230.
Lorenz, H. et al., "Crystallization of enantiomers", Chemical Engineering and Processing, vol. 45, (2006), pp. 863-873.
Ikariya et al. Organic Syntheses, "Preparation of Optically Active (R,R)-Hydrobenzoin From Benzoin or Benzil 1,2-Ethanediol, 1,2-diphenyl-, (1R,2R)" vol. 82, p. 10-17 (2005); Coli. vol. 11, p. 17-24 (2009).
Corey et al. "Reduction of Carbonyl Compounds with Chiral Oxazaborolidine Catalysts: A New Paradigm for Enantioselective Catalysis and a Powerful New Synthetic Method" Angew. Chem. Int. Ed. 1998, 37, 1986-2012.
English translation of Japanese Office Action dated Sep. 17, 2013, issued in connection with Japanese Patent Application No. 2011-520493.
Abstract of Japanese Laid-open Patent Publication No. 2005-324082, Nov. 24, 2005.
Abstract of Japanese Laid-open Patent Publication No. Hei 02-19339, Jan. 23, 1990.
Schmid et al, "Chiral Resolutionof RR,SS-Hydrobenzoin by Liquid Chromatography Using Borate-Cyclodextrin Complexation", Journal of High Resolution Chromatography, 1998, 21(7) 414-416.

* cited by examiner

*Primary Examiner* — Venkataraman Balasubramanian
(74) *Attorney, Agent, or Firm* — Nixon & Vanderhye P.C.

(57) ABSTRACT

The present invention discloses a process for isolating enantiomer components from a mixture of enantiomers through particle-size-controlled crystallization, comprising the steps of: (a) forming a solution of a mixture of enantiomers (R) and (S) in a solvent in the absence of any further additives or agents; (b) seeding the solution of step (a) simultaneously or consecutively with seed crystals of enantiomer (R) and with seed crystals of enantiomer (S), wherein the seed crystals of enantiomer (R) differ in size and/or in quantity from the seed crystals of enantiomer (S) to allow separation of the crystals composed of a mixture enriched with enantiomer (R) from the crystals composed of a mixture enriched with enantiomer (S); (c) inducing simultaneous crystallization of enantiomer (R) and enantiomer (S); and (d) isolating crystals composed of a mixture enriched with enantiomer (R) from crystals composed of a mixture enriched with enantiomer (S) through size separation of the crystals, preferably through sieving, melting or sedimentation, in particular through sieving.

8 Claims, No Drawings

PROCESS OF ISOLATING ENANTIOMER COMPONENTS FROM ENANTIOMER MIXTURES BY PARTICLE-SIZE-CONTROLLED CRYSTALLIZATION

This application is a divisional of U.S. application Ser. No. 12/737,613 (pending), filed 28 Jan. 2011 (published as US 2011-0184169 A1), which is the U.S. national phase of International Application No. PCT/EP2009/059769, filed 28 Jul. 2009, which designated the U.S., and claims priority to EP Application No. 08013586.6, filed 29 Jul. 2008, the entire contents of each of which is hereby incorporated by reference.

TECHNICAL FIELD

The present invention relates to a process for isolating enantiomer components from a mixture of enantiomers through particle-size-controlled crystallization.

PRIOR ART

Isolation of enantiomers from a mixture of enantiomers is typically difficult because the enantiomers generally have identical chemical and physical properties, such as melting and boiling points, or other such properties typically used for separation. Moreover, they tend to crystallize as racemic crystals rather than as a conglomerate consisting of a mixture of pure enantiomer crystals which would be separable by preferential crystallization (also called resolution by entrainment). Thus, a common way today to obtain enantiomers is not through isolating individual enantiomers from a mixture, but rather through asymmetric synthesis of the enantiomer. The efficiency of such a synthesis is strongly depending on the chemical structure of the enantiomer and can suffer from lack of selectivity.

Techniques for isolating enantiomers in use today include various embodiments of chromatography, such as simulated moving bed chromatography (SMB) for example. Chromatography-based methods, however, to date are not capable of isolating enantiomers and/or cannot isolate some enantiomers economically in commercial quantities.

Various crystallization methods have been proposed for separating enantiomers from a mixture, including preferential crystallization, co-crystallization and emulsion-crystallization. Relevant prior art documents are as follows:

DE 2135717 describes a process for the purification of a component of a fluid mixture selected from aromatic hydrocarbons and impurities by crystallization in a cooling agent as well as a crystallization apparatus. The process does not involve the separation of enantiomers and comprises the production of an emulsion.

GB 796 343 discloses a process of purifying sulphuric acid by fractional crystallization. The process does not involve the separation of enantiomers and comprises the production of a dispersion/emulsion.

GB 865 311 relates to a process for continued resolution of racemic amino acids, i.e. D- and L-glutamic acid. First, the one enantiomer is crystallized and separated from the mother liquor. Then, the antipode isomer is crystallized and removed from the solution.

GB 1 455 710 is directed to the resolution of optically active isomers by selective seeding and crystallization. Again, first the one enantiomer is crystallized and separated from the mother liquor. Then, the antipode isomer is crystallized and removed from the solution.

EP 0 548 028 describes the purification of organic compounds from an aggregate mixture by crystallization by means of a three-phase system. The process comprises the production of a dispersion/emulsion.

EP 0 838 448 discloses a process for the separation of a mixture of enantiomers by means of at least one resolving agent. The process requires the presence of at least one resolving agent.

WO 96/06080 relates to a process for the separation of the enantiomers of a bicyclic lactam. First, the one enantiomer is crystallized and separated from the mother liquor. Then, the antipode isomer is crystallized and removed from the solution.

WO 97/32644 is directed to a process of separating a desired substance from an aggregate mixture, in which process a three-phase dispersion is formed. The process comprises the production of a dispersion/emulsion.

WO 99/12623 describes a separation process for separating a desired substance from an aggregate mixture in an emulsion. The emulsion further contains one or more surface active agents, such as solubilizers, surfactants and/or dispersants. The process comprises the production of a dispersion/emulsion.

WO 00/53283 discloses a process for isolating enantiomer components from a mixture of enantiomers through co-crystallization by means of specific chiral or achiral co-crystallization agents. The process requires the presence of co-crystallization agents and requires that the enantiomers crystallize as a conglomerate.

WO 00/54865 relates to a process of purifying substances through emulsion crystallization with recycling (recovery) of emulsion. The process does not involve the separation of enantiomers and comprises the production of a dispersion/emulsion.

WO 04/089917 is directed to a process for resolving amines derived from dihydro-1,3,5-triazines from the corresponding racemic mixture. The process makes use of chiral HPLC in supercritical phase and chiral reagents, such as chiral acids.

The citation of any reference in this application is not an admission that the reference is prior art to this application.

DESCRIPTION OF THE INVENTION

The present invention has the object to provide a novel process of isolating enantiomer components from an enantiomer mixture, preferably a racemate, which does not comprise the production of a dispersion or emulsion and/or does not require the presence of a resolving agent, surface active agent (surfactant) and/or co-crystallization agent.

The object of the present invention has surprisingly been solved in one aspect by providing a process for isolating enantiomer components from a mixture of enantiomers through particle-size-controlled crystallization, comprising the steps of:

(a) forming a solution of a mixture of enantiomers (R) and (S) in a solvent in the absence of any further additives or agents;

(b) seeding the solution of step (a) simultaneously or consecutively with seed crystals of enantiomer (R) and with seed crystals of enantiomer (S), wherein the seed crystals of enantiomer (R) differ in size and/or in quantity from the seed crystals of enantiomer (S) to allow separation of the crystals composed of a mixture enriched with enantiomer (R) from the crystals composed of a mixture enriched with enantiomer (S);

(c) inducing simultaneous crystallization of enantiomer (R) and enantiomer (S); and (d) isolating crystals composed of a mixture enriched with enantiomer (R) from crystals composed of a mixture enriched with enantiomer (S) through size separation of the crystals, preferably through sieving, melting or sedimentation, in particular through sieving.

The terms "particle-size-controlled crystallization" and "isolating crystals composed of a mixture enriched with enantiomer (R) from crystals composed of a mixture enriched with enantiomer (S) through size separation of the crystals" in the meaning of the present invention refers to a crystallization-based separation of enantiomers with concomitant control of the particle size of the enantiomer crystals to be finally separated. To achieve this goal, (seed) crystals of enantiomer (R) need to differ sufficiently in size from (seed) crystals of enantiomer (S) thereby allowing separation by a simple size separation process, such as sieving using a sieve with a defined pore size which lets the fine crystals of the mixture of the enriched one enantiomer pass through and withholds the larger crystals of the mixture of the enriched other enantiomer by choice of the particle diameter of the respective seed crystals the necessary sufficient difference in size between both enantiomer crystal types can be adjusted.

The term "solvent" in the meaning of the present invention refers to pure solvents or solvent mixtures, such as water, organic solvents, aliphatic or aromatic hydrocarbons, alcohols, ethanol, methanol, propanol, isopropanol, n-butanol, tert-butanol, esters, ketones, acetone, or methylethylketon or mixtures thereof. Preferred solvent is ethanol. The choice of the solvent is depending on the relative solubilities of the enantiomers to be separated in this solvent.

The term "in the absence of any further additives or agents" in connection with "solvent" in the meaning of the present invention refers to solvents or solvent mixtures as defined herein, which do not contain one or more additional substances not being the enantiomers to be separated. Such not contained additional substances are, for instance, solvent additives, solubilizers, surfactants and dispersants as disclosed in WO 99/12623 and WO 97/32644, and resolving agents as disclosed in EP 0 838 448.

The induction of (simultaneous) crystallization of enantiomer (R) and enantiomer (S) can be achieved by standard techniques known in the art, for instance, by supersaturation, whereby an excess amount of enantiomer (R) and enantiomer (S) is dissolved by means of ultrasound or employing elevated temperatures. Or supersaturation is achieved by cooling down the solution containing both enantiomers. The supersaturated solution is seeded simultaneously or consecutively with seed crystals of enantiomer (R) and with seed crystals of enantiomer (S), wherein the seed crystals of enantiomer (R) differ in size and/or in quantity from the seed crystals of enantiomer (S). The use of controlled cooling conditions by the following crystallization step allows mainly crystal growth of the seed crystals and avoids spontaneous nucleation. As the end-temperature of the crystallization process is reached, the suspension is simply filtered on a filter ("Nutsche" or centrifuge). The isolated crystals are dried and finally sieved in order to separate the fine crystals composed of a mixture enriched with the one enantiomer from the larger crystals composed of a mixture enriched with the other enantiomer.

In another aspect, the object of the present invention has surprisingly been solved by providing above described process further comprising the steps of:

(e) dissolving the isolated crystals composed of a mixture enriched with the enantiomer (R) in a solvent in the absence of any further additives or agents and, separately therefrom, dissolving the isolated crystals composed of a mixture enriched with the enantiomer (S) in a solvent in the absence of any further additives or agents;

(f) seeding the solution enriched with enantiomer (R) with seed crystals of enantiomer (R) and, separately therefrom, seeding the solution enriched with enantiomer (S) with seed crystals of enantiomer (S);

(g) inducing crystallization of enantiomer (R) and, separately therefrom, inducing crystallization of enantiomer (S);

(h) isolating the crystals composed of a mixture further enriched with enantiomer (R) and, separately therefrom, isolating the crystals composed of a mixture further enriched with enantiomer (S).

In a preferred embodiment, the herein disclosed processes are provided, wherein the mixture of enantiomers (R) and (S) is a racemate of enantiomers (R) and (S), preferably forming a conglomerate.

In another preferred embodiment, the herein disclosed processes and preferred embodiments are provided, wherein the "mother liquor" solution remaining after step (d) and/or step (h) is recycled as solution in step (a) and/or the solution in step (a) is replenished prior to step (b) and the entire process is repeated. This recycling results in significant improvements in yield.

In a further preferred embodiment, the herein disclosed processes and preferred embodiments are provided, wherein the solvent in step (a) and/or step (e) is selected from the group consisting of: water, organic solvents, aliphatic or aromatic hydrocarbons, alcohols, ethanol, methanol, propanol, isopropanol, n-butanol, tert-butanol, esters, ketones, acetone or methylethylketon or mixtures thereof. Preferred is ethanol.

In yet another preferred embodiment, the herein disclosed processes and preferred embodiments are provided, wherein the mixture of enantiomers (R) and (S) is a mixture of ((R)-(4-Imino-6-methyl-1,4,5,6-tetrahydro-[1,3,5]triazin-2-yl)-dimethylamine (1) and ((S)-(4-Imino-6-methyl-1,4,5,6-tetrahydro-[1,3,5]triazin-2-yl)-dimethylamine (2), preferably a racemate of ((R)-(4-Imino-6-methyl-1,4,5,6-tetrahydro-[1,3,5]triazin-2-yl)-dimethylamine (1) and ((S)-(4-Imino-6-methyl-1,4,5,6-tetrahydro-[1,3,5]triazin-2-yl)-dimethylamine (2).

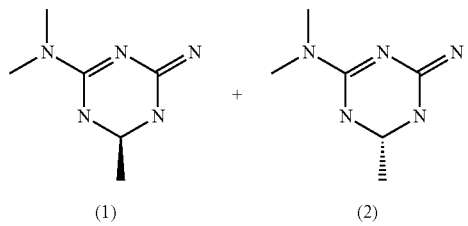

(1)          (2)

In yet another preferred embodiment, the herein disclosed processes and preferred embodiments are provided, wherein ((R)-(4-Imino-6-methyl-1,4,5,6-tetrahydro-[1,3,5]triazin-2-yl)-dimethylamine and ((S)-(4-Imino-6-methyl-1,4,5,6-tetrahydro-[1,3,5]triazin-2-yl)-dimethylamine are present as hydrochloride salts.

Above two enantiomers co-exists with their different mesomers as depicted below. These mesomers are intended to be comprised by the scope of the present invention.

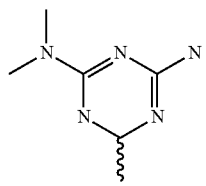 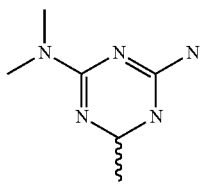

AutoNom Name:
6,N*2*,N*2*-Trimethyl-
1,6-dihydro-
[1,3,5]triazine-2,4-diamine

AutoNom Name:
6,N*4*,N*4*-Trimethyl-
1,6-dihydro-
[1,3,5]triazine-2,4-diamine

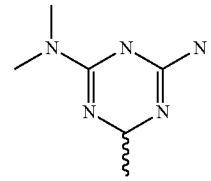 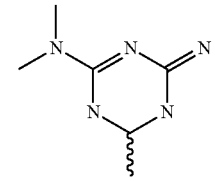

AutoNom Name:
6,N,N-Trimethyl-3,6-dihydro-
[1,3,5]triazine-2,4-diamine

AutoNom Name:
(4-Imino-6-methyl-
1,4,5,6-tetrahydro-
[1,3,5]triazin-2-yl)-
dimethyl-amine In another aspect, the object of the present invention has surprisingly been solved by providing ((R)-(4-Imino-6-methyl-1,4,5,6-tetrahydro-[1,3,5]triazin-2-yl)-dimethylamine hydrochloride obtainable by the herein disclosed processes and preferred embodiments.

The triazin derivative compounds were named using AutoNom 2000 software (ISIS™/Draw 2.5; MDL).

In yet another preferred embodiment, the herein disclosed processes and preferred embodiments are provided, wherein the mixture of enantiomers (R) and (S) is a mixture of (1R,2R)-1,2-diphenyl-ethane-1,2-diol usually called (R,R)-hydrobenzoin (3) and (1S,2S)-1,2-diphenyl-ethane-1,2-diol usually called (S,S)-hydrobenzoin (4), preferably a racemate of (3) and (4).

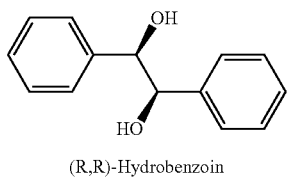

(R,R)-Hydrobenzoin (3)

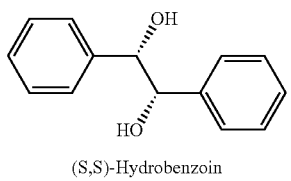

(S,S)-Hydrobenzoin (4)

In another aspect, the object of the present invention has surprisingly been solved by providing (R,R)-Hydrobenzoin and/or (S,S)-Hydrobenzoin separately obtainable by the herein disclosed processes and preferred embodiments.

The contents of all cited references are hereby incorporated by reference in their entirety. The invention is explained in more detail by means of the following examples without, however, being restricted thereto.

EXAMPLES

Example 1

Isolation of enantiomers of (4-Imino-6-methyl-1,4,5,6-tetrahydro-[1,3,5]triazin-2-yl)-dimethylamine hydrochloride First Step—Particle-Size-Controlled-Crystallization:

1.1 kg ((R)-(4-Imino-6-methyl-1,4,5,6-tetrahydro-[1,3,5]triazin-2-yl)-dimethylamine hydrochloride/((S)-(4-Imino-6-methyl-1,4,5,6-tetrahydro-[1,3,5]triazin-2-yl)-dimethylamine hydrochloride racemate is dissolved in 5.5 kg Ethanol and the resulting solution is carefully stirred with a metallic propeller (angle ~45°, 150 rpm) and cooled down to 55° C. for seeding. 70 g ((R)-(4-Imino-6-methyl-1,4,5,6-tetrahydro-[1,3,5]triazin-2-yl)-dimethylamine hydrochloride crystals (sieve-size >300 µm) are added, and it is then isothermally stirred for 30 min before seeding with 15 g ((S)-(4-Imino-6-methyl-1,4,5,6-tetrahydro-[1,3,5]triazin-2-yl)-dimethylamine hydrochloride crystals (sieve-size <59 µm) and further 30 min stirring at 55° C.

The mixture is finally carefully cooled down with a slow programmed ramp:

−0.07 K/min until 45° C., fast heating up to 50° C. and 30 min stirring at 50° C.
−0.07 K/min until 30° C., fast heating up to 35° C. and 30 min stirring at 35° C.
−0.07 K/min until 10° C., fast heating up to 15° C. and 30 min stirring at 15° C.
−0.07 K/min until −15° C.

As soon as the final temperature of −15° C. is reached, the complete suspension is filtered on a suction filter, the resulting filter cake is washed with 550 g cold (5-7° C.) ethanol and finally dried 2 days under vacuum (~200 mbar) at room temperature in a dessicator.

1011.6 g dried crystals are isolated corresponding to a yield of 92% (seed-crystals not considered).

The dried crystals are subsequently sieved (Table 1):

TABLE 1

| Fraction | Sieve values [µm] | m [g] | Yield [%] | HPLC contents [%] R-enantiomer | S-enantiomer |
|---|---|---|---|---|---|
| 07EW075.1 | — | 1005.76 | 100 | — | — |
| 07EW075.2 | >900 | 10.24 | 1.0 | 65.1 | 34.8 |
| 07EW075.3 | 500-900 | 131.95 | 13.1 | 87.1 | 12.7 |
| 07EW075.4 | 200-500 | 180.91 | 18.0 | 83.4 | 16.3 |
| 07EW075.5 | 100-200 | 117.43 | 11.7 | 50.7 | 48.9 |
| 07EW075.6 | <100 | 565.23 | 56.2 | 34.2 | 65.5 |

Second Step—Thermodynamically Controlled Crystallization of ((R)-(4-Imino-6-methyl-1,4,5,6-tetrahydro-[1,3,5]triazin-2-yl)-dimethylamine hydrochloride-enriched Fraction:

The fractions 07EW075.3 and 07EW075.4 (Table 1) are mixed affording 312.4 g crystals with the following composition (((R)-(4-Imino-6-methyl-1,4,5,6-tetrahydro-[1,3,5]triazin-2-yl)-dimethylamine hydrochloride 85.2%, ((S)-(4-Imino-6-methyl-1,4,5,6-tetrahydro-[1,3,5]triazin-2-yl)-dimethylamine hydrochloride 14.8%). These crystals are dissolved in 3755 g ethanol at 55° C. under stirring (200 rpm). The resulting solution is cooled down to 48° C. and seeded with 13.7 g ((R)-(4-Imino-6-methyl-1,4,5,6-tetrahydro-[1,3,5]triazin-2-yl)-dimethylamine hydrochloride crystals.

The mixture is first stirred 1 h at 46° C. and then cooled down to 0° C. with a controlled ramp of −0.2 K/min. The resulting suspension is directly filtered at 0° C. on a suction filter, the cake washed with 150 g cold ethanol (5-7° C.) and finally dried under vacuum in a dessicator at room temperature.

This affords 206.4 g ((R)-(4-Imino-6-methyl-1,4,5,6-tetrahydro-[1,3,5]triazin-2-yl)-dimethylamine hydrochloride crystals with an ee=93.8% (composition: ((R)-(4-Imino-6-methyl-1,4,5,6-tetrahydro-[1,3,5]triazin-2-yl)-dimethylamine hydrochloride 96.6%, ((S)-(4-Imino-6-methyl-1,4,5,6-tetrahydro-[1,3,5]triazin-2-yl)-dimethylamine hydrochloride 3.1%).

The yield of the second step is 66.1% (seed-crystals not considered).

The same process is carried out with the ((S)-(4-Imino-6-methyl-1,4,5,6-tetrahydro-[1,3,5]triazin-2-yl)-dimethylamine hydrochloride-enriched fraction in a similar fashion in order to increase the process yield.

Example 2

Isolation of Enantiomers of Hydroxybenzoin

First Step—Particle-Size-Controlled-Crystallization:

20 g (R,R)-hydrobenzoin/(S,S)-hydrobenzoin racemate is dissolved in 80 g Ethanol and the resulting solution is carefully stirred with a teflon propeller (angle ~45°, 180 rpm) and cooled down to 34.4° C. for seeding. 1 g (S,S)-hydrobenzoin crystals (sieve-size >500 μm) are added, the mixture is then isothermally stirred for 1 h before seeding with 0.2 g (R,R)-hydrobenzoin crystals (sieve-size <59 μm) and further 1 h stirring at 34° C.

The mixture is finally carefully cooled down with a slow programmed ramp:
−0.05 K/min until 25.5° C., fast heating up to 27.4° C. and 30 min stirring at 27.4° C.
−0.05 K/min until 15.3° C., fast heating up to 17.7° C. and 30 min stirring at 17.7° C.
−0.05 K/min until 5.7° C., fast heating up to 7.8° C. and 30 min stirring at 7.8° C.
−0.05 K/min until −13.6° C.

As soon as the final temperature of −13.6° C. is reached, the complete suspension is filtered on a suction filter, the resulting filter cake is washed with 5 g cold (−12° C.) ethanol and finally dried 24 h under vacuum (~200 mbar) at room temperature in a dessicator.

16.9 g dried crystals are isolated corresponding to a yield of 84.5% (seed-crystals not considered).

The dried crystals are subsequently sieved (Table 2):

TABLE 2

| Fraction | Sieve values [μm] | m [g] | Yield [%] | HPLC contents [%] R-enantiomer | S-enantiomer |
|---|---|---|---|---|---|
|  | — | 16.62 | 100 | — | — |
| 09EW047.1 | >500 | 6.90 | 41.5 | 91.15 | 8.85 |
| 09EW047.2 | 300-500 | 3.68 | 22.1 | 53.30 | 46.70 |
| 09EW047.3 | 200-300 | 3.67 | 22.1 | 22.41 | 77.59 |
| 09EW047.4 | 100-200 | 1.89 | 11.4 | 12.63 | 87.37 |
| 09EW047.5 | <100 | 0.48 | 2.9 | 6.43 | 93.57 |

Second Step—Thermodynamically Controlled Crystallization of (S,S)-hydrobenzoin Enriched Fraction:

The fraction 09EW047.1 (Table 2) composed of 6.6 g crystals with the following composition ((S,S)-hydrobenzoin 91.2%, (R,R)-hydrobenzoin 8.8%), is dissolved in 26.4 g ethanol at 63° C. under stirring (220 rpm). The resulting solution is cooled down to 52° C. and seeded with 0.05 g (S,S)-hydrobenzoin crystals. The mixture is first stirred 1 h at 52° C. and then cooled down to 0° C. with a controlled ramp of −0.2 K/min. The resulting suspension is directly filtered at 0° C. on a suction filter, the cake washed with 5 g cold ethanol (0° C.) and finally dried under vacuum in a dessicator at room temperature for 20 h. This affords 4.7 g (S,S)-hydrobenzoin crystals with an ee=99.8% (composition: (S,S)-hydrobenzoin 99.9%, (R,R)-hydrobenzoin 0.1%) corresponding to an overall yield of 47% for (S,S)-hydrobenzoin over the two-steps process (seed-crystals not considered). With consideration of seed-crystals, the process offers an overall yield of 42.5% for (S,S)-hydrobenzoin (ee=99.8%).

Third Step—Thermodynamically Controlled Crystallization of (R,R)-Hydrobenzoin-Enriched Fraction:

The fractions 09EW047.3, 09EW047.4 and 09EW047.5 (Table 2) are mixed affording 4.65 g crystals with the following composition ((S,S)-hydrobenzoin 18.4%, (R,R)-hydrobenzoin 81.6%). These crystals are dissolved in 18.6 g ethanol at 64° C. under stirring (220 rpm). The resulting solution is cooled down to 54.5° C. and seeded with 0.05 g (R,R)-hydrobenzoin crystals. The mixture is first stirred 1 h at 54° C. and then cooled down to −1° C. with a controlled ramp of −0.2 K/min. The resulting suspension is directly filtered at −1° C. on a suction filter, the cake washed with 5 g cold ethanol (0° C.) and finally dried under vacuum in a dessicator at room temperature for 20 h.

This affords 3.0 g (R,R)-hydrobenzoin crystals with an ee=97.4% (composition: (S,S)-hydrobenzoin 1.3%, (R,R)-hydrobenzoin 98.7%) corresponding to an overall yield of 30% for (R,R)-hydrobenzoin over the two-steps process (seed-crystals not considered). With consideration of seed-crystals, the process offers an overall yield of 29.3% for (R,R)-hydrobenzoin (ee=97.4%). Remark: The mother liquors of all three steps and the almost racemic sieve-fraction 09EW047.2 of the first step could be recycled and reused together with fresh racemate in a new particle-size-controlled-crystallisation cycle in order to reduce losses and consequently increase the process yield.

The invention claimed is:
1. A process for isolating enantiomer components from a mixture of enantiomers through particle-size-controlled crystallization, comprising the steps of:
(a) forming a solution of a mixture of enantiomers (R) and (S) in a solvent in the absence of any further additives or agents;
(b) seeding the solution of step (a) simultaneously or consecutively with seed crystals of enantiomer (R) and with seed crystals of enantiomer (S), wherein the seed crystals of enantiomer (R) differ in size and/or in quantity from the seed crystals of enantiomer (S) to allow separation of the crystals composed of a mixture enriched with enantiomer (R) from the crystals composed of a mixture enriched with enantiomer (S);
(c) inducing simultaneous crystallization of enantiomer (R) and enantiomer (S); and
(d) isolating crystals composed of a mixture enriched with enantiomer (R) from crystals composed of a mixture enriched with enantiomer (S) through size separation of the crystals,
wherein the mixture of enantiomers (R) and (S) is a mixture of ((R)-(4-Imino-6-methyl-1,4,5,6-tetrahydro-[1,3,5]triazin-2-yl)-dimethylamine (1) and ((S)-(4-Imino-6-methyl-1,4,5,6-tetrahydro-[1,3,5]triazin-2-yl)-dimethylamine (2),

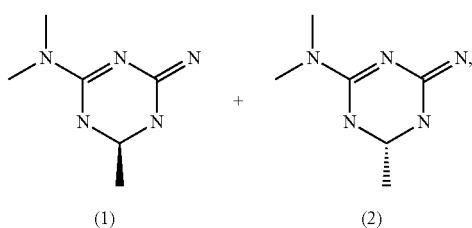

wherein the enantiomers are present as a salt selected from the group consisting of the 2,4-dichlorophenyl acetate, the chloroacetate, the hydrochloride, the propionate and the succinate salts.

2. The process as claimed in claim 1, further comprising the steps of:
(e) dissolving the isolated crystals composed of a mixture enriched with the enantiomer (R) in a solvent in the absence of any further additives or agents and, separately therefrom, dissolving the isolated crystals composed of a mixture enriched with the enantiomer (S) in a solvent in the absence of any further additives or agents;
(f) seeding the solution of enantiomer (R) with seed crystals of enantiomer (R) and, separately therefrom, seeding the solution of enantiomer (S) with seed crystals of enantiomer (S);
(g) inducing crystallization of enantiomer (R) and, separately therefrom, inducing crystallization of enantiomer (S);
(h) isolating the crystals composed of a mixture further enriched with enantiomer (R) and, separately therefrom, isolating the crystals composed of a mixture further enriched with enantiomer (S).

3. The process as claimed in claim 1 or 2, wherein the mixture of enantiomers (R) and (S) is a racemate of enantiomers (R) and (S).

4. The process as claimed in claim 1, wherein the "mother liquor" solution remaining after step (d) is recycled as solution in step (a) and/or the solution in step (a) is replenished prior to step (b) and the entire process is repeated.

5. The process as claimed in claim 1, wherein the solvent in step (a) is selected from the group consisting of: water, organic solvents, aliphatic or aromatic hydrocarbons, alcohols, ethanol, methanol, propanol, isopropanol, n-butanol, tert-butanol, esters, ketones, acetone or methylethylketon or mixtures thereof.

6. The process as claimed in claim 1, wherein said enantiomers are present as hydrochloride salts.

7. The process as claimed in claim 2, wherein the "mother liquor" solution remaining after step (h) is recycled as solution in step (a) and/or the solution in step (a) is replenished prior to step (b) and the entire process is repeated.

8. The process as claimed in claim 2, wherein the solvent in step (e) is selected from the group consisting of: water, organic solvents, aliphatic or aromatic hydrocarbons, alcohols, ethanol, methanol, propanol, isopropanol, n-butanol, tert-butanol, esters, ketones, acetone or methylethylketon or mixtures thereof.

* * * * *